United States Patent [19]

Chu et al.

[11] Patent Number: 5,006,464
[45] Date of Patent: Apr. 9, 1991

[54] DIRECTED FLOW DIAGNOSTIC DEVICE AND METHOD

[75] Inventors: Albert E. Chu, Hillsborough; Peter K. Chun, South San Francisco; Siu C. C. Yeung, San Mateo, all of Calif.

[73] Assignee: E-Y Laboratories, Inc., San Mateo, Calif.

[21] Appl. No.: 103,845

[22] Filed: Oct. 1, 1987

[51] Int. Cl.$^5$ .................... G01N 33/53; G01N 31/22; G01N 33/553
[52] U.S. Cl. .................................. 435/7.1; 435/7.92; 435/805; 435/810; 436/518; 436/525; 436/528; 436/531; 436/165; 436/170; 436/807; 436/808; 422/55; 422/56; 422/58; 422/101
[58] Field of Search .............. 435/7, 805, 810, 7.1, 435/7.92; 436/518, 528, 525, 531, 165, 170, 807, 808; 422/55, 56, 58, 60, 101

[56] References Cited

U.S. PATENT DOCUMENTS

| | | | |
|---|---|---|---|
| 3,888,629 | 6/1975 | Bagshawe | 436/541 X |
| 4,366,241 | 12/1982 | Tom et al. | 435/7 |
| 4,632,901 | 12/1986 | Valkers et al. | 435/805 X |
| 4,670,381 | 6/1987 | Frickey et al. | 436/501 X |
| 4,756,884 | 7/1988 | Hillman et al. | 435/810 X |
| 4,775,636 | 10/1988 | Moeremans et al. | 436/518 |
| 4,777,021 | 10/1988 | Wertz et al. | 422/101 |

Primary Examiner—Esther L. Kepplinger
Assistant Examiner—Carol A. Spiegel
Attorney, Agent, or Firm—Flehr, Hohbach, Test, Albritton & Herbert

[57] ABSTRACT

Am improved device and method for analyte assay in liquid samples, wherein a porous membrane with an immobilized receptor which is capable of directly or indirectly binding to the analyte is separated from a body of absorbent material capable of absorbing the liquid sample by a septum capable of substantially separating the porous membrane from the absorbent body while substantially directing the flow of the liquid sample from the porous membrane to the absorbent body.

23 Claims, 3 Drawing Sheets

DIRECTED FLOW DIAGNOSTIC DEVICE AND METHOD

TECHNICAL FIELD

The present invention relates to devices and methods for analyte assay in liquid samples. More particularly, the invention relates to devices and methods utilizing immobilized specific binding receptors for analytes in liquid samples derived from biological specimens.

BACKGROUND OF THE INVENTION

There has long been an interest in the development of assay systems which can determine the presence or amount of specific substances in samples derived from biological specimens. Over the past two decades, immunoassays, which employ naturally occurring receptors directed to specific target substances, have provided valuable diagnostic tools for detecting substances of clinical significance. There are numerous immunoassays in the prior art in which one component of an immunological pair, e.g., an antigen or antibody, is detected or measured by using the complementary partner labelled with a tag which provides a detectible signal.

In one assay technique, known as competitive binding technique, the substance to be detected competes with a labelled reagent of the same substance for a limited number of receptor sites. For example, for the detection of an unknown amount of a selected antigen in a liquid sample, a known amount of the labelled antigen is added to the sample and then contacted with receptor antibody specific for the antigen. The amount of labelled antigen which binds to the antibody is inversely proportional to the amount of the unknown antigen in the sample.

In another assay, known as a sandwich assay, receptor antibody is bound to a solid surface and the selected antigen in the sample binds to that antibody. A second labelled antibody capable of binding to the bound antigen is then reacted with the antigen to form an immobilized reaction product. The label in the reaction product is detected as an indication of the presence of the antigen in the sample.

For the detection or measurement of an antigen using a sandwich technique, antisera have been used for many years for both the labelled antibody and for the receptor antibody on the surface. More recently, monoclonal antibodies have been used in place of the antisera in such assay. In one such system, described in Wada, et al., Clin. Chem., 28(9):1986–1966 (1982), the receptor antibody was directed to one subunit of a particular antigen, hCG, while an enzyme-labelled monoclonal antibody was directed to another subunit. In this assay, the receptor antibody is immobilized on the inside of the test tube to which the sample was added.

Reaction on a solid surface can be relatively slow because the contact between the immobilized reagent and the analyte in the sample is limited. The assay time has been reduced by immobilizing the receptor antibody within a porous membrane, exposing the antibody molecules in a three-dimensional matrix. In many such systems the liquid sample containing the target antigen is drawn through the membrane into an underlying absorbent material. One such system, disclosed for use in a competitive binding assay, is U.S. Pat. No. 3,888,629. Other systems disclosed for use in competitive or sandwich assays include U.S. Pat. Nos. 4,246,339, 4,366,241, 4,632,901.

However, most such assay systems allow the deposition of particulate matter on the surface of the filter, thus obscuring the results when using, for example, a chromophoric label. In addition, these systems do not provide a means for controlling the flow rate of the liquid in the sample. The system of U.S. Pat. No. 4,623,461 attempts to address these problems by forcing the liquid sample to flow transversely to the periphery of the filter by having the absorbent material associated only with the peripheral area of the filter. It is claimed that this system results in decreased deposition of particulate matter on the filter surface and improved separation of the analyte.

Unfortunately, as the frontal surface area of the transverse cross-section of the membrane is quite small, the liquid will necessarily take longer to pass completely through into the absorbent. In addition, the flow through characteristics could not be altered without changing to a different membrane.

Thus, it would be desirable to improve the sensitivity and separation of a membrane-bound receptor assay while controlling the fluid flow characteristics of the assay system.

It would also be desirable to control the fluid flow characteristics of a system by means other than the thickness and pore size of the membrane which immobilizes the reactant.

Disclosure of the Invention

This invention provides an assay device and method for detecting an analyte in a liquid sample, particularly a sample derived from biological specimen. The device of the present invention includes a porous reaction membrane with an immobilized receptor which is capable of directly or indirectly binding to the target substance. The device also includes a body of absorbent material located adjacent to the porous reaction membrane which is capable of absorbing the liquid sample. Positioned between these components is a septum, typically in the form of a sheet having one or more selected ports, capable of substantially separating the porous membrane from the absorbent body while directing the flow of the liquid sample from the porous membrane to the absorbent body.

The liquid sample is assayed to form a detectible reaction product on the membrane. In preferred assay embodiments, the liquid sample is biologically derived (e.g., urine or serum) and is suspected to include as the target substance, typically an antigen, antibody, or hapten capable or being bound by the receptor immobilized on the membrane.

In the detection of a selected antigen in a sandwich assay, a receptor antibody reagent (to which the antigen binds) is immobilized on the membrane. Target antigen in a fluid sample is bound to the receptor antibody. A second reagent, soluble labelled antibody capable of binding the target antigen, then reacts with the bound antigen to form a detectible reaction product on the membrane. These reactions can be simultaneous or sequential.

In a preferred embodiment, the device comprises a liquid impermeable membrane septum or sheet substantially separating the porous membrane from the absorbent body. This septum will be provided with channels or ports located so as to direct the liquid flow preferentially toward or away from the center of the porous membrane.

In another preferred embodiment, the septum comprises a body of porous material in at least one of the channels of the impermeable membrane septum. This body will provide a channel or conduit to enhance liquid flow between the porous membrane and the absorbent body only at the points of contact.

In a further preferred embodiment, the receptor reagent is concentrated in at least one defined region, such as a dot on the membrane, and the detectible reaction product is formed at the dot. For example, referring to a sandwich assay for a selected antigen, the receptor antibody is immobilized at a dot on the membrane to bind the antigen. The bound antigen then reacts in turn with a labelled antibody capable of binding to the bound antigen. Multiple dots using antibodies (or antigens) specifically reactive with different antigens (or antibodies) may also be employed to simultaneously assay different antigens in the sample.

In a still further preferred embodiment, the receptor reagent is immobilized on a porous membrane comprising nitrocellulose backed with paper or other material such as polyester or fiberglass.

DESCRIPTION OF THE PREFERRED EMBODIMENTS

This invention provides a novel and improved assay device and method for detecting an analyte or target substance in a fluid sample, particularly a sample derived from a biological specimen. The device of the present invention includes a porous reaction membrane with an immobilized receptor which is capable of directly or indirectly binding to the target substance. The device also includes a body of absorbent material located adjacent to the porous membrane and capable of absorbing the liquid sample. Positioned between these components is separating means in the form of a septum or sheet capable of substantially separating the porous membrane from the absorbent body while substantially directing the flow of the liquid sample for the porous membrane to the absorbent body through ports or channels through the septum.

Figure 1:
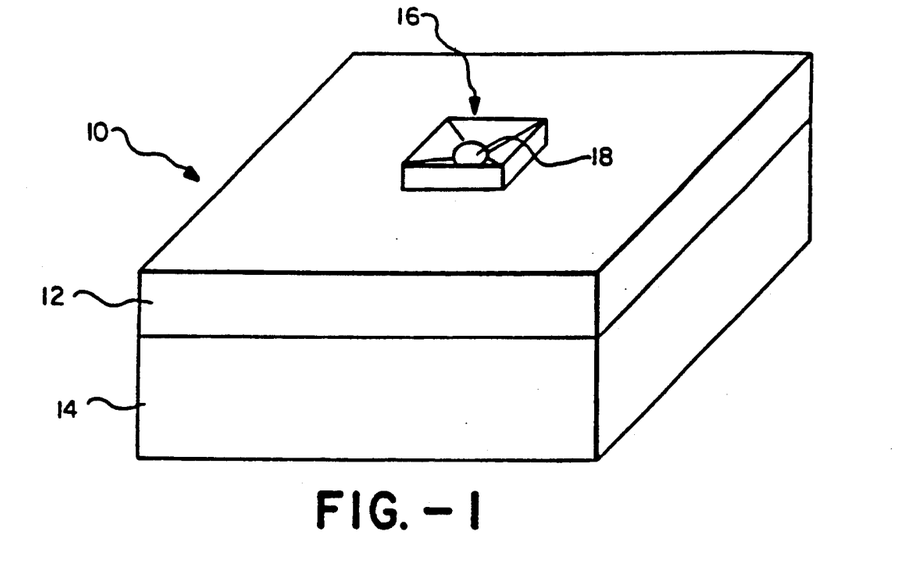
FIG. 1 is a perspective view of an assay device according to the present invention.

Referring now to the drawings, FIG. 1 depicts a representative assay device 10 according to the present invention. While the device is provided with a rectangular shape, any other appropriate shape may be employed and provided with an opening means for receiving and temporarily storing liquid which can conveniently be in the shape of an inverted frustoconical well bounded by a wall.

Figures 2, 3A, 3B, 3C:
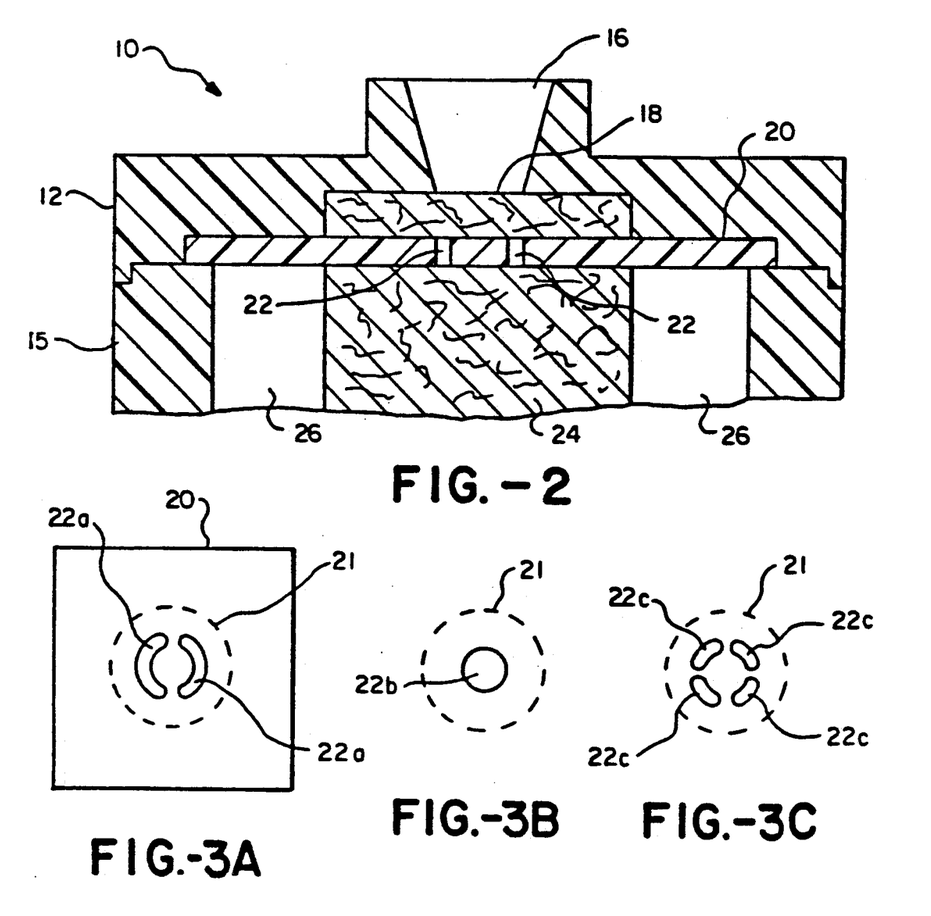
FIG. 2 is a cross-sectional view, with portions broken away, of an assay device according to the present invention.
FIGS. 3A, 3B and 3C are plan views of alternative embodiments of a septum of the device of FIG. 2.

The device of the present invention is disclosed in greater detail in FIG. 2, which depicts a vertical cross-section of the device of FIG. 1. As depicted therein, the device is illustrated in the form of container means defining a hollow receiving space or chamber 26. The boundaries of this space are provided herein by two components, 14 and 12, referred to herein for convenience as the base and cover, respectively. These components are suitably formed of a disposable plastic material such as polycarbonate polyethylene, polypropylene, polystyrene or polyvinyl chloride, or of a durable material such as a metal (e.g., aluminum) which permits reuse of device 10, if desired.

The receiving space 26 is shown to contain a body of absorbent material 24 separated from porous reaction membrane means 18 by a septum 20, whose functions are described in greater detail below. As shown, cover 12 includes well 16 bounded by a liquid retaining ring or wall conveniently shaped to receive the liquid sample and facilitate its contact with the membrane 18. By selectively matching the size of well 16 with receiving space 26 and absorbent body 24, the operation of the present apparatus can be simplified so that, for example, the entire liquid sample or optional wash liquid can be placed in well 16 as a single step of the operation.

As illustrated, membrane means 18 includes a porous reaction membrane with an externally visible upper surface. The reaction membrane may be of any type capable of immobilizing reaction product of the reagents and sample component without adversely affecting the reaction, and permits passage of the remainder of the liquid sample or of a washing solution. Suitable membranes may be formed of any material capable of immobilizing the receptor reagent employed in the practice of the present invention, such as nylon, glass fibers, or other natural or synthetic materials which can be coupled directly or indirectly to the selected receptor. The porosity of the membrane preferably varies from about 0.2 to about 12 microns.

However, as a presently preferred embodiment, membrane means 18 comprises paper-backed nitrocellulose, or other types of nitrocellulose membranes with similar characteristics. This embodiment comprises a nitrocellulose membrane backed with porous paper similar to filter paper. A representative example is commercially available under the tradename BAC-T-KOTE by Schleicher and Schuell. This preferred membrane is substantially more durable than nitrocellulose alone and can be employed without any other support component. Also, it provides enhanced sensitivity to the reaction. Also, polyester supported nitrocellulose may be used such as supplied under the name NITRO-PLUS by Micron Separation, Inc.

As described below, in a typical system, a binding reagent is first immobilized on the membrane. The reagent reacts with and captures the predetermined target substance of the liquid sample to be assayed. Such reagent, typically an immunological protein such as an antibody or antigen, can be immobilized directly or indirectly onto such membranes, such as nitrocellulose, by either adsorption or by covalent bonding.

The depth or thickness of the membrane is selected so that an adequate amount of binding reagent can be immobilized to capture the sample component. However, the thickness should not be so great as to cause undue delay of the passage of the liquid sample through the membrane.

The absorbent body 24 of the present device can employ any of the known and conventionally employed absorbent materials which serve to draw liquid through a porous membrane, such as, for example, by capillary action. Useful known materials include cellulose acetate fibers, polyester, polyolefin or other such materials. It has also been found convenient to use layers of commercially available filter paper, or even toilet paper, which can be selected to provide sufficient volume to absorb the liquid employed during the assay of the present invention.

As seen in FIG. 2, substantially isolating membrane means 18 from absorbent body 24 is separating means in the form of septum 20. Septum 20 will have outer dimensions appropriate for the container employed in the device of the present invention. For example, septum 20 as shown in FIG. 3A, can be provided comprising a membrane of sufficient size so that it is retained in a position and is sealed by the opposition of cover 12 to base 14 in FIG. 2. In this manner, a seal is formed which prevents liquid flow around reaction membrane 18 and channels flow through the openings or ports 22 in septum 20. Suitable septum membranes may be formed of any material which is substantially impermeable to liquid and, desirably, is not reactive with or harmed by the reagents employed in the practice of the present invention, such as membranes of plastic material such as polyethylene, polypropylene, polystyrene, polyvinyl chloride, or the like.

Referring further to FIG. 3A, septum impermeable membrane 20 will have located thereon a zone 21 whose boundary is an imaginary line which approximates the lower dimension of frustoconical well 16. This is the zone through which liquid would tend to flow from the lower surface of porous membrane 18 to absorbent body 24. Located within or toward the center of zone 21 in the septum embodiment of FIG. 3A are passages or ports 22a, which are openings which are filled with absorbent permeable material through which liquid may flow. In a particular embodiment of the present invention, as illustrated in FIGS. 3A and 3C, these passages 22a and 22c, respectively, are radially spaced from the center of the immobilized receptor or typically in the center of zone 21 to direct the flow of liquid away from the immobilized receptor center and towards the periphery. As an alternative, in FIG. 3B the device is provided with a passage 22b proximal to the center of the immobilized receptor which will tend to direct the liquid flow toward the center of zone 21. This phenomenon will be described more fully below.

Figure 4:
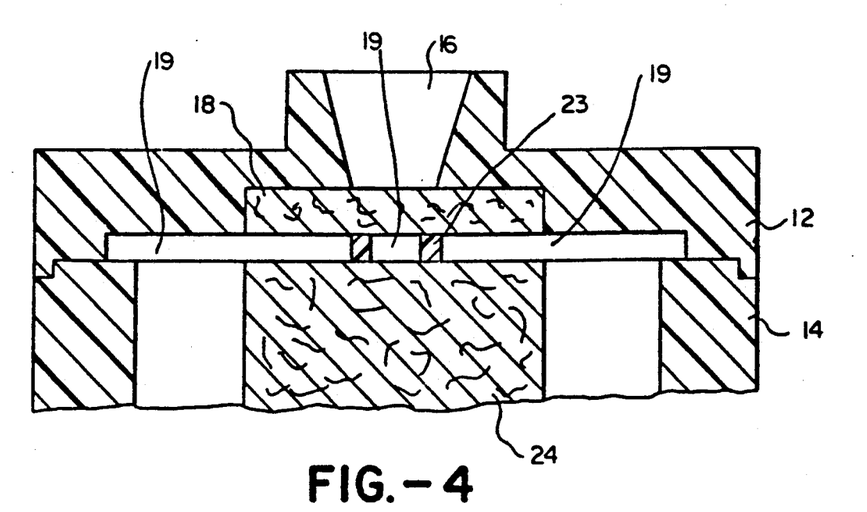
FIG. 4 is a cross-sectional view, with portions broken away, of another assay device according to the present invention.

FIGS. 4 and 5A-C illustrate alternative septum means 20 using various combinations of an annular ring 23 of absorbent material, which can be the same or a different material as absorbent body 24. This annular ring 23 of FIG. 4 provides the only separation between membrane 18 and body 24 and permits selected liquid flow contact between limited portions of the facing surfaces of the absorbent body. The ring is retained in place by pressure between membrane 18 and body 12. In effect, the septum or separation means is the open area 19 around and within ring 23 which serves as the port through the open septum.

Figure 5A:
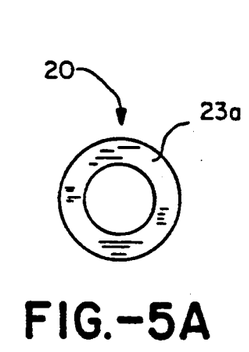
FIGS. 5A, 5B and 5C are alternative embodiments of septums.

FIG. 5A illustrates a top view of ring 23a in the form used in the device of FIG. 4. The outer dimension of annular ring 23a will generally approximate the boundary dimension of zone 21 or less. In this embodiment, liquid flow through porous membrane 18 will tend to be directed away from the center of zone 21 and through the passage provided by the body of ring 223a.

Figure 5B:
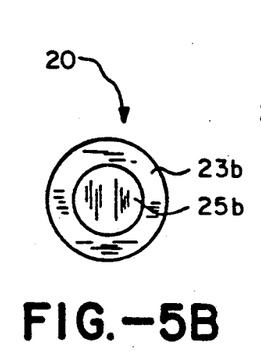

Turning to FIG. 5B, as an alternative embodiment, septum 20 is in the form of ring 23b which includes an internal portion or disk 25b of substantially liquid-impermeable material, which can be the same as the sheet of septum 20 described above. Disk 25b would tend to enhance the flow direction capabilities of annular ring 23b by preventing inadvertent contact between center portions of membrane means 18 and absorbent body 24, thus preventing resultant undirected liquid flow. Here, the separating means is the combination of the open area outside ring 23b and disk 25b.

Figure 5C:
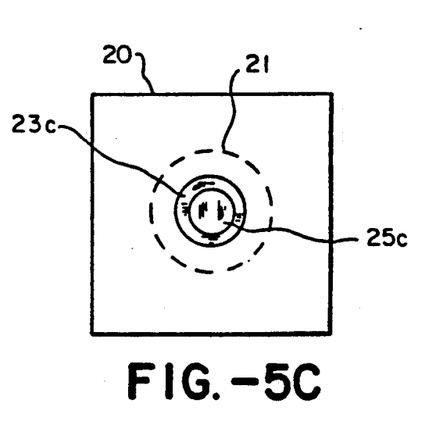

As a further alternative embodiment, septum 20 is shown in FIG. 5C as a membrane of liquid impermeable material similar to that provided in the embodiment of FIG. 3A. Here, absorbent material is inserted into impermeable septum sheet 20 and retains impermeable disk 25c. This complete septum provides further control over the liquid flow in the device of the present invention.

Figure 6:
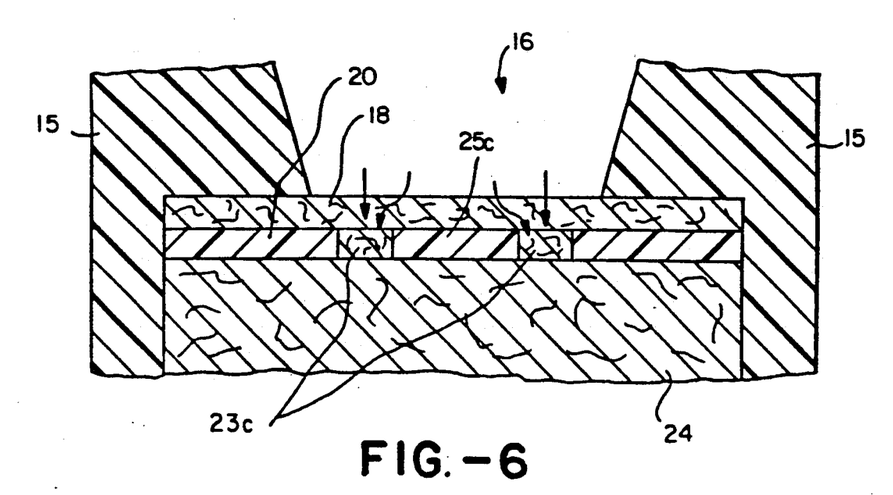
FIGS. 6, 7, 8 and 9 are cross-sectional views, with portions broken away, of assay devices according to the present invention.

Referring to FIG. 6, another embodiment of the device includes a unit or device housing or boundary 15 which defines a relatively wide rim to funnel the liquid. Also, membrane 18 and absorbent body 24 extend across the entire interior of the open space. The septum 20 is of the same type illustrated in FIG. 5C. Here, as illustrated by the arrows, the liquid flows through reaction membrane 18 preferentially away from the center of the immobilized receptor, typically located at the center of the upper surface of membrane 18 exposed to the liquid. This is caused by impermeable septum 20 surrounding ring of absorbent material 23c which, in turn, retains impermeable disk 25c in its center. Thus, the liquid on the upper surface of membrane 18 can only flow through absorbent material 23c resulting in flow away from the center of the immobilized receptor.

Figure 7:
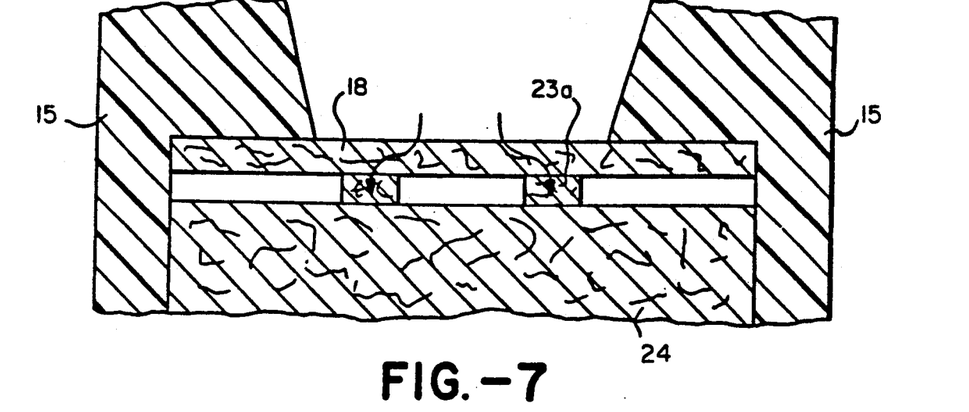

The device of FIG. 7 is similar to that of FIG. 6 except for the septum which is similar to that of FIG. 4. Here, the septum comprises ring 23a with a total open area to the center and outside of the ring. Effective fluid contact between membrane 18 and absorbent material 24 is made via ring 23a through which the liquid flows as in the pattern of the device of FIG. 6. Like FIG. 4, this illustrates that an open space can, in effect, constitute the separating means if the liquid has a path through an absorbent material port which is far less resistant to flow.

Figure 8:
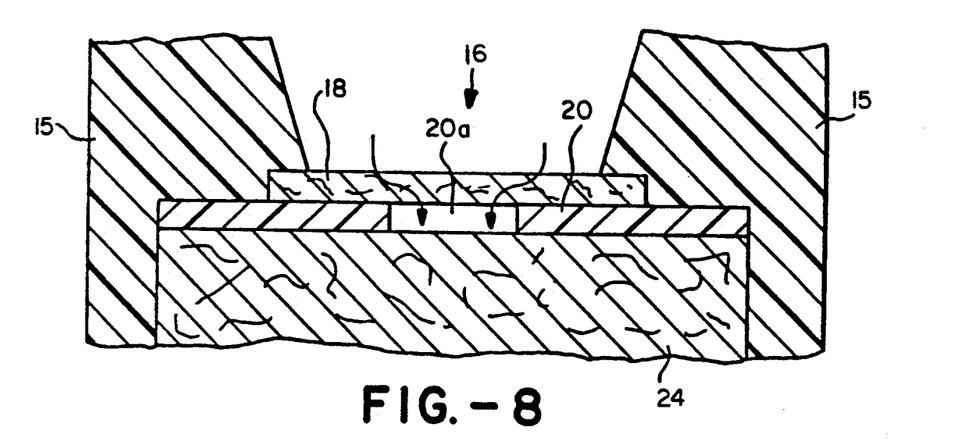

Referring to FIG. 8, a device is illustrated similar to that of FIG. 6 but with certain important differences. Membrane 18 is in the form of a disk of a smaller diameter than that of membrane 18 in FIG. 7. The most significant difference is that septum 20 is designed to cause the liquid to flow towards the center of the immobilized receptor (or center of membrane 18) rather than away from it. This is accomplished by forming port 20a in an area directly below the immobilized receptor center. In the illustrated embodiment, port 20a is a round disk shape with a diameter substantially less than that of the perimeter of the exposed upper surface of membrane 18. Here port 20a is open but, as with the other embodiments, absorbent material can be placed in the opening to serve as the port.

Figure 9:
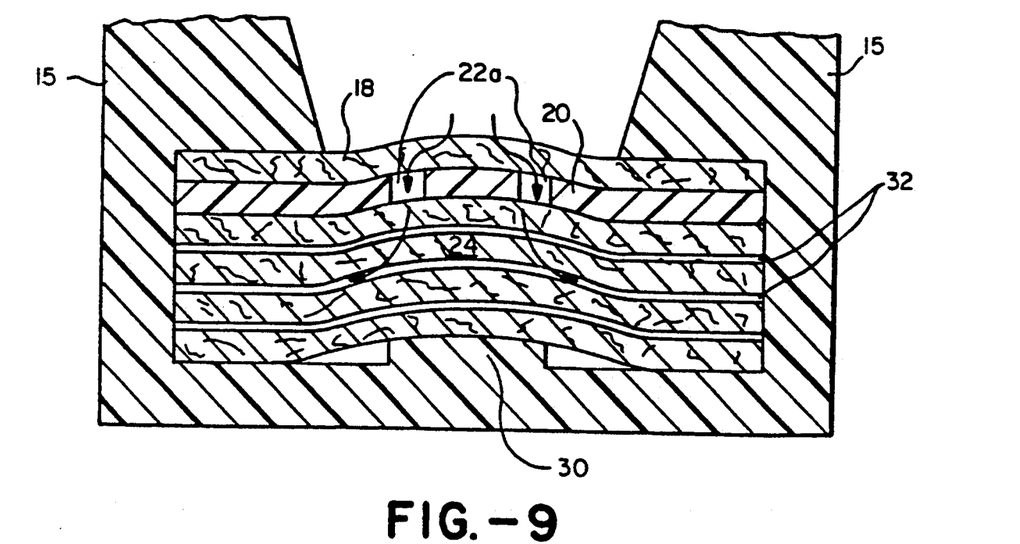

Another embodiment of the invention is illustrated in FIG. 9. As with the other devices, here the body of absorbent material 24 is pliable. The device further includes platform means, suitably in the form of pedestal or plug 30, which projects upwardly into the absorbent material towards the center of the immobilized receptor. As illustrated, plug 30 preferably is of sufficient height so that, when pressed against the absorbent material body 24, sufficient upward pressure is applied against the absorbent material to cause flexing of the flexible impermeable sheet 20, into a slightly convex configuration and to correspondingly modify the unflexed shape of the port means toward the center. In addition, where the absorbent material comprises multiple layers of fibers 32 such as filter paper or paper towels, the layers above plug 30 tend to loosely fall away like butterfly wings. In this manner, space is created between the filter paper in the form of channels, providing improved flow in comparison to tightly compressed absorbent paper.

An important feature of the invention is the ability to optimize the kinetics of the reaction by directing flow of the tested sample either away from the center of the immobilized receptor or towards it by a selection of the location and type of ports through the septum. The flow rate is adjusted to be fast for convenience of the user, but slow enough that the target substance will be captured. Also, it is desirable to flow away from the center for certain high viscosity samples, such as serum, which could otherwise tend to clog the reaction membrane. Conversely, for low viscosity sample, such as urine, where clogging is not a problem and where there may be a low concentration of target substance, it is desirable to flow the liquid towards the center of the reaction membrane In operation, the assay device of the present system broadly is used to determine the presence of analyte in a liquid sample, employing at least one reagent to form a detectible product on membrane 18 as an indication that the analyte is present in the sample. The liquid sample is contacted on one side of membrane means 18 by introduction through the opening in well 16. After permeating membrane 18, the liquid is drawn therethrough by and into absorbent body 24. However, due to the operation of the septum 10 of the present device, the flow rate and direction of this liquid can be controlled, as the liquid flow between lower surface of membrane 18 and the surface of absorbent body 24 is constrained and directed either through passages 22 or the conduit provided by absorbent member 23. The operation of assays in accordance with the present invention will be described in further detail below.

For the specific devices of FIGS. 2-7 and 9, the flow is directed away from the center of the immobilized receptor. In a preferred embodiment, the receptor is located in a small region (e.g. a dot) of the total available upper surface of membrane 18. Here, it is preferable that the sample flow primarily in a pattern proximal to the outer boundaries of this small region. In this manner, most (preferably substantially all) of the liquid sample contacts the sample perimeter rather than being concentrated at the center of the region as it would be if the port through the septum was an open center. The latter form of port can lead to clogging of the center for a viscous fluid such as serum. On the other hand, the port(s) are formed so that substantially all of the sample contacts the receptor region rather than a major portion bypassing it around the region's periphery as it would if no septum were used at all. For this purpose a preferable form of the septum port is a continuous or discontinuous ring, or their equivalent that produces this annular flow. By this adjustment of the flow pattern, the sensitivity of the system for low concentration samples (e.g HIV antibody in serum) is increased without clogging of the membrane.

For the device of FIG. 8, flow is directed toward the center of the immobilized receptor, e.g. in the form of a dot, by use of an open center septum. Preferably, the open center has an outer perimeter dimensioned to correspond to the outer perimeter of the dot. This embodiment is particularly useful to increase the kinetics and sensitivity for samples of low viscosity and having a target substance at a lower concentration.

The system is particularly applicable to an immunoassay wherein the sample component is one component of an immunological pair including antigens, antibodies, or haptens. The immunological pair includes two components which immunologically bind to each other. Specific immunological pairs include antigens and their antibodies (monoclonal antibodies or polyclonal antibodies), biologically functional haptens and their antibodies, enzymes and their substrates, hormones and their receptors, vitamins and their receptors, biotin and either avidin or an antibody to biotin, and lectin and its specific binding mono, di- or trisaccharide.

For simplicity of description, the system will be described with respect to immunoassays using the antigen-antibody immunological pair. The liquid sample is biologically derived, (e.g., urine or serum) and the one reagent comprises a labelled antigen or antibody.

Referring first to a sandwich assay for the detection of antigen, the one reagent is a labelled antibody specific for the predetermined antigen in the sample. This system uses a second reagent, a capture antibody also specific for the predetermined antigen, immobilized on membrane 18 prior to addition of the liquid sample to the device. The techniques of immobilizing proteins such as monoclonal or polyclonal antibodies to solid surfaces such as membrane 18 without deactivation are well known. See e.g., Schuurs U.S. Pat. No. 3,551,555 and Hendry et al., J. Immun. Methods, 35 1980, 285. For plastic materials such as nylon, such proteins may be immobilized by covalent bonding, e.g., as described in U.S. Pat. No. 3,720,760. The amount of protein immobilized per unit area of nylon is greater than that for nitrocellulose.

The labelled antibody or antigen described with respect to the sandwich assay may be any of the conventional types including radioactive, enzyme, or a metal complex label which are conjugated to the antibody. Formation of conjugates between such immunological substances and labels are well known, e.g., (a) radioactive labels—U.S. Pat. No. 3,646,346, Hunter et al., Nature 142 (1962), 945, (b) enzyme labels—U.S. Pat. Nos. 3,654,090, 3,791,931 and 3,817,838, Wilson et al., Immunoflourescense and Related Staining Techniques, Knapp., W. et al., Eds. L. Sevier-North Holland, Bio-Medical Press, New York-Amsterdam, 1978, pp. 215-224; (c) fluorescent quencher labels—U.S. Pat. No. 3,996,345; (d) radioactive labels—U.S. Pat. No. 4,062,733; (e) fluorescent or enzyme labels U.S. Pat. No. 4,067,959; (f) chemiluminesct labels—U.S. Pat. No. 4,104,029; (g) non-enzymatic catalyst label—U.S. Pat. No. 4,160,645; (h) enzyme pair labels—U.S. Pat No. 4,233,402, chemically induced fluorescent labels—U.S. Pat. No. 4,720,450; and (i) enzyme non-ionic charge labels—U.S. Pat. No. 4,287,300. In addition, the labels disclosed in U.S. Pat. No. 4,366,241 may be employed. Also, colloidal gold labels are discussed in detail hereinafter.

Colloidal gold conjugates useful for probes such as cytochemical markers are well known for microscopy. See, e.g., *Scanning Electron Microscopy*, 1981, II, pp. 9-31, "Immunocytochemistry" Eds. Polak, J. N., et al., Bristol, London, Boston (1982) pp. 82-112, and *Journal of Neuroscience Methods*, 7(1983), pp.1-18. Colloidal gold particle markers are simple to use in comparison to other conventional markers. For example, they do not require instruments necessary for detection of other markers such as radioactive isotopes. Furthermore, unlike enzymes, they do not require the additional step of adding substrate. However, they have not been used extensively for commercial immunoassay kits, perhaps because of their low level of visibility using conventional techniques for mixing reactants. For example, the sensitivity of an assay using colloidal gold conjugates in a previous membrane system has been thought to be insufficient to provide the desired level of sensitivity. It has been found that by directing the flow of the liquid sample and reagents through the membrane, the sensitivity is so improved that colloidal gold particle conjugates are useful reagents for immunoassay kits without the need to use expensive microscopes.

If the sensitivity of the gold-immunological reagent conjugate is insufficient, even with the increase of the present system, a technique for enhancing the sensitivity of the gold complex may be employed such as disclosed in Holgate, C. S., et al., J. Histochem. Cytochem 31:938 (1983) and in Dancher, G, et al., J. Histochem. Cytochem 31:1394 (1983). This system is an "indirect" technique employing an immunological reagent, immunoglobulin, absorbed to colloidal gold. The gold particles are revealed by a silver precipitation reaction. In essence, the silver enhancement takes advantage of the catalytic effect of gold to catalyze the photographic physical developer process converting silver ion to silver metal. Suitable colloidal gold or gold sol particle size is from 3 nm to 150 nm. This immuno gold-silver staining method may have an enhanced sensitivity of up to 200-fold in comparison to the use of the gold particles without silver staining.

The effect of directed flow is particularly apparent when the immunological reagent is concentrated at a specific region, such as a dot on the membrane, as described below. In that instance, the immobilized antibody is only deposited at that one dot. In conventional techniques, only the antigen in the sample in an imaginary column above the dot contacts the antibody. The remaining antigen in the sample passes through the membrane without such contact. In contrast, directing the flow of liquid sample containing the antigen causes exposure of significantly more antigen to the immobilized antibody on the membrane with the above advantageous results. This principle of increased effeciency applies to any of the conventional immunoassays with respect to which the present system may be employed. Also, the increased effeciency or interaction increases the local concentration of reactants which, in turn, increases the reaction kinetics.

The present invention is also applicable to the competitive binding technique. In such system for the detection of antigen in a liquid sample, the corresponding member of the immunological pair, i.e., antibody is immobilized on to the membrane surface. Antigen labelled in the manner described above of the same immunological character as the antigen analyte to be detected in the sample is contacted with the immobilized antibody on the membrane. The immobilized antibody is in limited supply, and so a competition is set up between the antigen in the sample and the labelled antibody. Thus, the signal emitted from the label is inversely proportional to the amount of antigen in the sample. As with the sandwich assay, the competitive binding assay may be performed by reversing the roles of the antigen and antibody. In this instance, the immobilized member of the immunological pair is the antigen for the detection of antibody in the sample which competes with labelled antibody.

The immunoassays which have been described are the sandwich assay and the competitive binding assay. It should be understood that the system is also useful for other immunoassays such as, for example, described in U.S. Pat. No. 4,366,241.

The substances to be analyzed include a wire variety of biologically derived substances, e.g., proteins. The following is a list of some of these substances. (The listed substances also include immunologically reactive antibodies, and fractions of the substances).

Immunoglobulins
  IgE
  IgA
  IgM
  IgD
Microorganisms
Aerobacter aerogenes
Aerobic Spore-Forming Bacilli
  *Bacillus anthracis*
  *Bacillus subtilis*
  *Bacillus cereus*
Anaerobic Spore-forming Bacilli
  *Clostridium botulinum*
  *Clostridium tetani*
  *Clostridium perfringens*
Brucellae
  *Brucella melitensis*
  *Brucella abortus*
  *Brucella suis*
Chlamydia
  *Chlamydia trachomatis*
Corynebacteria
  *Corynebacterium diptheriae*
  *Escherichia coli*
Fungi
  *Cryptococcus neoformans*
  *Histoplasma capsulatum*
  *Coccidioides immitis*
  *Candida albicans*
  *Mucor corymbifer (Absidia corymbifera)*
Hemophilus-Bordetella group
  *Hemophilus influenzae*
  *H. ducreyi*
  *H. hemophilus*
  *H. aegypticus*
  *H. parainfluenzae*
*Klebsiella pneumoniae*
Mycobacteria
  *Mycobacterium tuberculosis hominis*
  *Mycobacterium bovis*
  *Mycobacterium avium*
  *Mycobacterium laprae*
  *Mycobacterium paratuberculosis*
Mycoplasmas
  *Mycoplasma pneumoniae*
  *Mycoplasma hominis*
Neisseriae
  *Neisseria meningitidis*

*Neisseria gonorrheae*
Other Pathogens
　*Listeria monocytogens*
Pasteurellae
　*Pasteurella pestis*
　*Pasteurella multocida*
Pneumococci
　*Diplococcus pneumoniae*
*Pseudomonas aeruginosa*
Rickettsiae (bacteria-like parasites)
　*Rickettsia prowazekii*
　*Rickettsia mooseri*
　*Rickettsia rickettsii*
　*Rickettsia conori*
　*Rickettsia australis*
　*Rickettsia tsutsugamushi*
　*Rickettsia burnetii*
*Salmonella choleraesus*
*Salmonella typhimurtum*
*Salmonella typhosa*
*Shigella arabinotardo*
*Shigella boydii*
*Shigella dysenteriae*
*Shigella flexneri*
*Shigella schmitzii*
*Shigella sonnei*
Staphylococci
　*Staphylococcus aureus*
　*Staphylococcus albus*
Streptococci
　*Streptococuccus pyogenes*
　Groups B, C, D, F, G
The Spirochetes
　*Treponema pallidum*
　*Borrelia recurrentis*
　*Leptospira icterohemorrhagiae*
　*Leptospira canicola*
*Toxoplasma gondii*
Peptide and Protein Hormones
Corticotropin (ACTH)
(adrenocorticotropic hormone)
Follicle-stimulating hormone
Luteinizing hormone
　(interstitial cell-stimulating hormone)
Parathyroid hormone
Prolactin
Chorionic Gonadotropin
Insulin
Glucagon
Relaxin
Somatropin
Triiodothyronine
Thyrocalcitonin
Thyroxine
Tissue Hormones
　Angiotensin I and II
　Bradykinin
　Gastrin
　Human placental lactogen
　Secretin
Peptide Hormones
　Oxytocin
　Vasopressin
Viruses
Adenoviruses
Arboviruses
　Eastern Equine Encephalitis Virus
　Western Equine Encephalitis Virus
　Sindbis Virus
　Semliki Forest Virus
　St. Louis Encephalitis Virus
　California Encephalitis Virus
　Colorado Tick Fever Virus
　Yellow Fever Virus
　Dengue Virus
Hepatitis
　Hepatitis A Virus
　Hepatitis B Virus
Herpes Viruses
　Herpes simplex, Types I and II
　Varicella (Chicken pox)
　Cytomegalovirus
Myxoviruses
　Influenza (A, B, and C)
　Parainfluenza (1-4)
　Mumps virus
　Newcastle Disease Virus
　Measles Virus
　Canine Distemper Virus
　Respiratory Syncytial Virus
　Rubella Virus
Picronaviruses
　Poliovirus
　Coxsackievirus
　Echoviruses
　Rhinoviruses
Pox Viruses
　Vaccinia
　Molluscum contagiosum The system is also applicable to other assay systems which are not categorized as immunoassays, e.g., the detection of unknown DNA sequences. For example, liquid sample containing the unknown DNA sequence is passed through the membrane and immobilize on the membrane as by contact with DNA previously immobilized on the membrane. Then, a labelled DNA probe passed in a liquid through the membrane. If hybridization occurs, the labelled DNA probe will be retained in detectible form on the membrane surface. This system is described in Polsky-Cynkin, R., et al., Clin. Chem. 31/9, 1438 (1985).

As mentioned above, in a particularly effective assay, the immunological reagent is concentrated on at least one defined region on the membrane which appears as a dot but which actually extends through the membrane in a column of a diameter approximately equal to the dot. Referring to a sandwich or competitive binding techniques, this is accomplished by immobilizing the capture immunological reagent, e.g., antigen or antibody, only in such region by flowing the reagent to be immobilized through the membrane thickness. The reaction with the sample component and with the labelled reagent only occurs in that region.

The dot approach has certain advantages such as the performance of multiple simultaneous assays with a single device as described below. Also it provides a more distinctive end product signal since it is concentrated at a single region.

Another advantage of the dot approach is that it permits the simultaneous detection of multiple components in a sample. For example, with a single assay device, two different antibodies specific for predetermined different antigens can be immobilized on distinct spots on the membrane. The sample suspected of containing either one of the antigens is then contacted with the membrane and with labelled antibody specific for the two different membranes. A signal produced by the labels at one or the other of the dots indicates the presence or absence of one or both of the antigens. The dots may be distinguished from each other by their location or by an identification near each immobilized antibody dot. Thus, for example, if a color appears at the first dot but not the second, the first antigen but not the second antigen is present. If both dots appear, then both antigens are present, and if no dots appear, neither antigen is present. Alternatively, the label may be selected to produce different colors at each of the dots.

This system could be expanded to include the simultaneous detection of more than two components of the liquid sample by a corresponding number of immobilized immunological reagent on the membrane. In some instances, a first antibody is reactive with a particular subunit of a number of different antibodies. If a second antibody is specific for a subunit of one antigen only, such second antibody can be used as the immobilized antibody and a single labelled first antibody can be used as the universal labelled antibody for antigen of interest.

The standard protocols for the conventional immunoassays may be used in the present invention. For example, in a sandwich assay, the order of addition of the sample and labelled reagents may be simultaneous or sequential.

While monoclonal antibodies have known advantages and purity over polyclonal antibodies, either type of immunological reagent can be used in accordance with the present invention.

While the above system is described in terms of yes-no quantitative test, it should be understood that it is also suitable as semi-quantitative test using appropriate signals, such as colors, produced at different known concentrations of the component to be analyzed. Thus, for example, for the analysis of an antigen by a sandwich technique, the system can be run at progressive dilution to obtain an approximation of the color expected for a particular dilution. The unknown concentration of an antigen is compared to these colors to give an approximation of the concentration of antigen present in the sample.

Further disclosure of the nature of the present invention is provided by the following specific examples. It should be understood that the examples disclosed are not intended to limit the scope of the invention.

EXAMPLE 1

In this example, a device of the type shown in FIG. 8 is used in which a sample flows preferentially toward the center of the immobilized receptor. A sandwich immunoassay is illustrated for the antigen human chorionic gonadotropin (hCG) in a urine sample containing a known amount of hCG. Monoclonal and polyclonal antibodies were used for the immobilized reagent and for the labelled reagent, respectively. The labelled conjugate comprises a gold sol prepared in accordance with the procedure of Faulk, W. P., et al., Immunochem. 8:1081 (1981). Briefly summarized, 100 ml distilled water containing 0.01% chloro-auric acid solution is mixed with 4 ml of 1% trisodium citrate and boiled for 15 minutes. The solution turns from yellow to red at an optical density at 520 nm of about 1.

The bound immunological reagent is an anti-$\alpha$ subunit hCG monoclonal antibody supplied by Medix. A membrane 18 comprising paper-backed nitrocellulose (supplied by Schleicher and Schuell) is used. The anti-$\alpha$ hCG antibody is applied to the prewetted disk three times in amounts of 5 $\mu$ at a concentration of 1-2 mg/ml in a limited area of about 9 mm diameter. After drying, the inoculated disk is then incubated with a blocking solution containing 5% BSA and 0.01% sodium azide in phosphate buffered saline, in order to decrease non-specific binding with the nitrocellulose, and placed into the device described above.

Monoclonal anti-$\beta$ subunit hCG antibody (supplied by Medix) is conjugated in accordance with the procedure of Roth, supra, with this gold sol and is frozen in a $-50°$ F. temperature bath. Then it is freeze-dried.

A 140 $\mu$l urine sample is placed in well 16, onto the upper surface of membrane 18. The sample solution is then drawn by absorbent body 24 through membrane 18, either through passages 22.

As an example, during passage through membrane 18, the liquid flow is directed for the lower surface of membrane 18 through passageway 22a provided in septum means 20. In this way, the sensitivity of the assay is increased by causing the liquid to flow through the membrane transversely as well as vertically. In addition, the flow rate of the liquid is controlled by the size of the passageway 20a, allowing the development of an optimum incubation time for the assay reaction. This permits the visual reading of a red dot on the membrane using colloidal gold particles at antigen concentrations where this would not normally be possible.

In this example, 102 clinical urine specimens (51+ and 51−) were tested and correlated 100% with the clinical findings from the specimen source. The sensitivity level was determined to be 25 mIU hCG/ml.

EXAMPLE 2

In this instance, a device of the type shown in FIG. 9 was used in which sample flows preferentially away from the center of the immobilized receptor. A sandwich assay was performed in which antigen was immobilized on the membrane, an antibody analyte of a serum sample was to be analyzed, and the labelled antibody is a conjugate of an anti-antibody to the sample antibody labelled with colloidal gold formed in the manner described above. In this instance, the anti-antibody employed was *Staphlococcus aureus* A protein, which serves as a universal anti-antibody.

The antigen, HIV lysate (E. I. DuPont de Nemours, Wilmington, Del.) at 2 mg/ml in a DuPont buffer containing detergent and ethylene glycol was deposited onto a nitrocellulose membrane disk as described in Example 1. The blocking reaction was performed with 100 $\mu$l of the DuPont proprietary buffer, or an equivalent buffer containing 5% BSA, 0.05% TWEEN-20, 0.1% sodium azide and 10% goat serum in PBS.

A sample of the serum suspected of containing antibodies to the antigen is prepared by a 1:4 dilution with the DuPont buffer and 50 $\mu$ is placed is well 16 and allowed to flow through membrane 18 as described above. Then membrane 18 is washed with 50 $\mu$l of DuPont buffer of PBS. Thereafter 50 $\mu$l of the labelled Protein A (secondary antibody), at $OD_{520}$ of 3.5, is passed through the membrane in a similar fashion, followed by an additional 50 $\mu$l wash. A positive reaction is indicated by a distinct red dot on the membrane.

In this example, 200 samples (31+ and 169−) were tested and correlated 100% with the reported findings from the specimen source, as determined by DuPont ELISA. The positive samples were confirmed by Western Blot analysis.

Obviously, many modifications and variations of the present invention are possible after consideration of the present disclosure. It is therefore to be understood that within the scope of the appended claims, the invention may be practiced otherwise than as is specifically described.

What is claimed is:

1. An analytical apparatus for use in assays for the detection of a bindable target substance in a liquid sample suspected of containing such substance, comprising;
   (a) a reaction membrane which is liquid-permeable and porous and having an upper and lower surface, an exposed area of said upper surface having immobilized therein a receptor capable of directly or indirectly binding to the bindable target substance said immobilized receptor being concentrated in a limited region of said upper surface;
   (b) a body of absorbent material capable of absorbing a liquid, said body having a surface located adjacent to the lower surface of the reaction membrane;
   (c) separating means for substantially preventing liquid flow from the lower surface of the reaction membrane to the upper surface of the absorbent material body; and
   (d) port means through said separating means for substantially directing the flow of liquid from the lower surface of said reaction membrane through said separating means into said absorbent material body, said port means comprising at least one port containing liquid permeable material contacting said reaction membrane, said port means being of a substantially smaller cross-sectional area than said reaction membrane upper surface exposed area and being adapted to direct liquid flow downwardly through said reaction membrane with a radial flow component in a substantially horizontal plane either (1) radially away from the center of said immobilized receptor outwardly towards the periphery of said reaction membrane or (2) radially inwardly toward the center of said immobilized receptor;

whereby liquid sample applied to the upper surface of said reaction membrane will permeate in a selected flow pattern to its lower surface and be substantially directed to at least one selected portion of the reaction membrane.

2. The analytical apparatus of claim 1 wherein said reaction membrane comprises nitrocellulose.

3. The analytical apparatus of claim 2 wherein said nitrocellulose reaction membrane further comprises at least one liquid-permeable support material bonded in intimate contact therewith.

4. The analytical apparatus of claim 3 wherein said support material is paper, fiberglass or polyester.

5. The analytical apparatus of claim 1 in which said separating means comprises a liquid impermeable sheet.

6. The analytical apparatus of claim 1 in which said port means is spaced radially from the center of said immobilized receptor in a horizontal plane and serves to direct liquid flow radially outwardly away from the center of said immobilized receptor as the liquid flows downwardly through said reaction membrane.

7. The analytical apparatus of claim 6 in which said port means comprises a ring or a portion thereof spaced radially from the center of said immobilized receptor.

8. The analytical apparatus of claim 7 in which said port means is proximal to the periphery of said limited region.

9. The analytical apparatus of claim 1 in which said port means is disposed proximal to the center of said immobilized receptor surrounded by said separating means.

10. The analytical apparatus of claim 1 including sealing means serving to cause substantially all of the liquid sample contacting the upper surface of said porous membrane to flow through the membrane in an area bounded peripherally by said sealing means.

11. The analytical apparatus of claim 1 in which said absorbent material is pliable, said apparatus further comprising means defining said absorbent material and including a bottom wall, and platform means disposed on said bottom wall projecting upwardly into said absorbent material toward the center in a horizontal plane of said immobilized receptor.

12. The analytical apparatus of claim 11 in which said separating means comprises an impermeable flexible sheet and said platform means applies sufficient upward pressure against said absorbent material to flex said impermeable sheet and modify the unflexed shape of said port means.

13. The analytical apparatus of claim 12 in which said port means is radially spaced from the center of said immobilized receptor in a horizontal plane.

14. The analytical apparatus of claim 13 in which the interior of said absorbent material body is spread apart under the pressure created by said platform means creating channels, whereby liquid can flow through said channels outwardly from the center of said immobilized receptor in a horizontal plane as the liquid flows through the membrane.

15. The analytical apparatus of claim 1 in which said separating means consists essentially of a liquid impermeable sheet.

16. The analytical apparatus of claim 1 wherein said reaction membrane further comprises at least one liquid permeable support material bonded in intimate contact therewith disposed on the absorbent material body side of said reaction membrane.

17. An assay method for the detection of a bindable target substance in a liquid sample suspected of containing such substance, employing as an assay device an analytical apparatus comprising:
   (a) a reaction membrane which is liquid-permeable and porous and having an upper and lower surface, an exposed area of said upper surface having immobilized thereon a receptor capable of directly or indirectly binding to the bindable target substance said immobilized receptor being concentrated in a limited region of said upper surface of said reaction membrane;
   (b) a body of absorbent material capable of absorbing a liquid, said body having a surface located adjacent to the lower surface of the reaction membrane;
   (c) separating means for substantially preventing liquid flow from the lower surface of the porous reaction membrane to the upper surface of the absorbent material body; and
   (d) port means through said separating means for substantially directing the flow of liquid from the lower surface of said porous reaction membrane through said separating means into said absorbent material body, said port means comprising at least one port containing liquid permeable material contacting said reaction membrane said port means being of a substantially smaller cross-sectional area than said reaction membrane upper surface exposed area;

the method comprising applying the liquid sample, visibly labelled substance capable of specific binding to said receptor or target substance, and any additional reagents to the upper surface of said permeable reaction membrane whereby the applied liquid sample will permeate through said port means to the membrane lower surface and be substantially directed to at least one selected portion of the adjacent surface of said absorbent material body, said liquid flowing downwardly through said reaction membrane with a radial flow component in a substantially horizontal plane directed either (1) radially away from the center of said immobilized receptor outwardly towards the periphery of said reaction membrane or (2) radially inwardly toward the center of said immobilized receptor and thereafter detecting said visible labelled substance bound to said upper surface in order to detect the presence or absence of target substance in the liquid sample.

18. The method of claim 17 wherein said porous reaction membrane of said apparatus comprises nitrocellulose.

19. The method of claim 17 wherein said nitrocellulose porous membrane further comprises at least one support material bonded in intimate contact therewith.

20. The method of claim 19 wherein said support material is paper.

21. The method of claim 17 in which said separating means comprises a liquid impermeable sheet.

22. The method of claims 17 or 21 in which said means is radially spaced from the center of said immobilized receptor in a horizontal plane, and in which said liquid flows radially away from said center towards said port but contacts said receptor periphery on passing through said reaction membrane compared to said liquid flow pattern absent said separating means and port means.

23. The method of claims 17 or 21 in which said port means is disposed proximal to the center of said immobilized receptor, and in which said liquid flows inwardly in a direction from the periphery of said membrane toward said center on passing through said impermeable membrane compared to its flow pattern absent said separating means and port means.

* * * * *